(12) United States Patent
Patil et al.

(10) Patent No.: US 11,123,087 B1
(45) Date of Patent: Sep. 21, 2021

(54) VENTRICULAR GUIDE FOR VENTRICULOSTOMY

(71) Applicants: Arun Angelo Patil, Omaha, NE (US); Deepak Kumar Pandey, Andover, MA (US); Keith Bernardo, Woburn, MA (US)

(72) Inventors: Arun Angelo Patil, Omaha, NE (US); Deepak Kumar Pandey, Andover, MA (US); Keith Bernardo, Woburn, MA (US)

( * ) Notice: Subject to any disclaimer, the term of this patent is extended or adjusted under 35 U.S.C. 154(b) by 0 days.

(21) Appl. No.: 17/236,367

(22) Filed: Apr. 21, 2021

(51) Int. Cl.
*A61B 17/16* (2006.01)
*A61B 17/34* (2006.01)
*A61B 17/17* (2006.01)

(52) U.S. Cl.
CPC ...... *A61B 17/1695* (2013.01); *A61B 17/3403* (2013.01); *A61B 17/17* (2013.01); *A61B 17/1739* (2013.01); *A61B 17/3415* (2013.01); *A61B 2017/3405* (2013.01); *A61B 2017/3407* (2013.01)

(58) Field of Classification Search
CPC . A61B 17/17; A61B 17/1717; A61B 17/1732; A61B 17/1739; A61B 17/1796; A61B 17/1728; A61B 17/3403; A61B 17/3415; A61B 17/1757; A61B 17/1637; A61B 17/1671; A61B 2017/3405; A61B 2017/3407; A61B 2017/3409; A61B 2017/3411; A61B 2017/565; A61B 2017/564; A61B 2017/568
USPC .......................................................... 606/80
See application file for complete search history.

(56) References Cited

U.S. PATENT DOCUMENTS

| | | | |
|---|---|---|---|
| 9,814,497 B1* | 11/2017 | Al-Habib | A61B 17/1757 |
| 2012/0245587 A1* | 9/2012 | Fang | A61B 17/1757 606/80 |
| 2016/0038309 A1* | 2/2016 | Doyle | A61B 17/1757 606/96 |
| 2017/0135706 A1* | 5/2017 | Frey | A61B 17/1671 |

* cited by examiner

*Primary Examiner* — Marcela I. Shirsat
(74) *Attorney, Agent, or Firm* — Dennis L. Thomte; Thomte Patent Law Office LLC

(57) ABSTRACT

A ventricular guide for ventriculostomy which includes a curved base plate, an upstanding support member which extends upwardly from the base plate and an upper support member which extends transversely from the upper end of the upstanding member. A first tubular guide, having a bore extending therethrough, is secured to one end of the upper support member. A second tubular guide, having a bore extending therethrough is secured to the other end of the upper support member. The bores of the tubular guides may have a drill bit, needle or catheter extending downwardly therethrough.

21 Claims, 3 Drawing Sheets

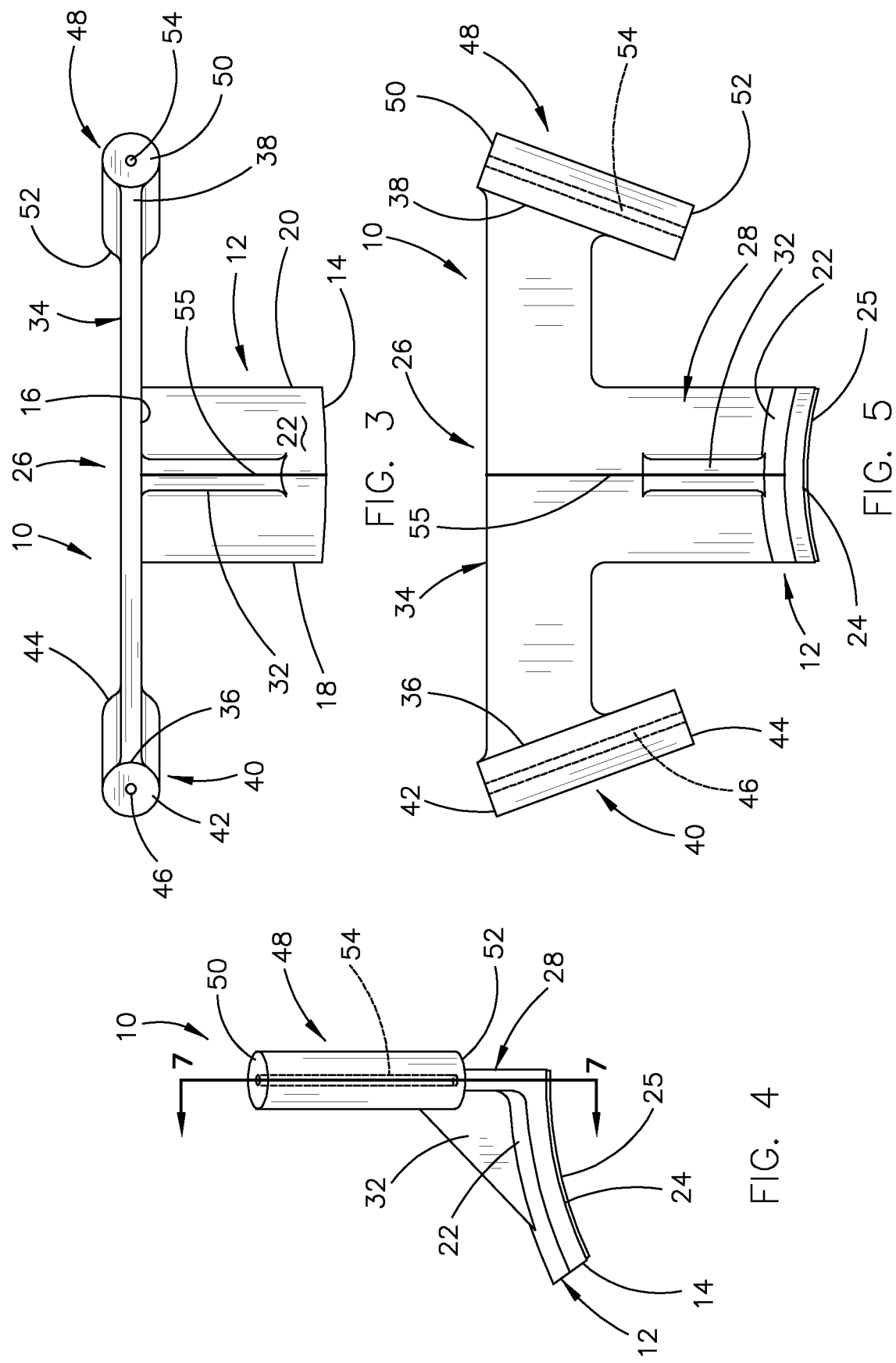

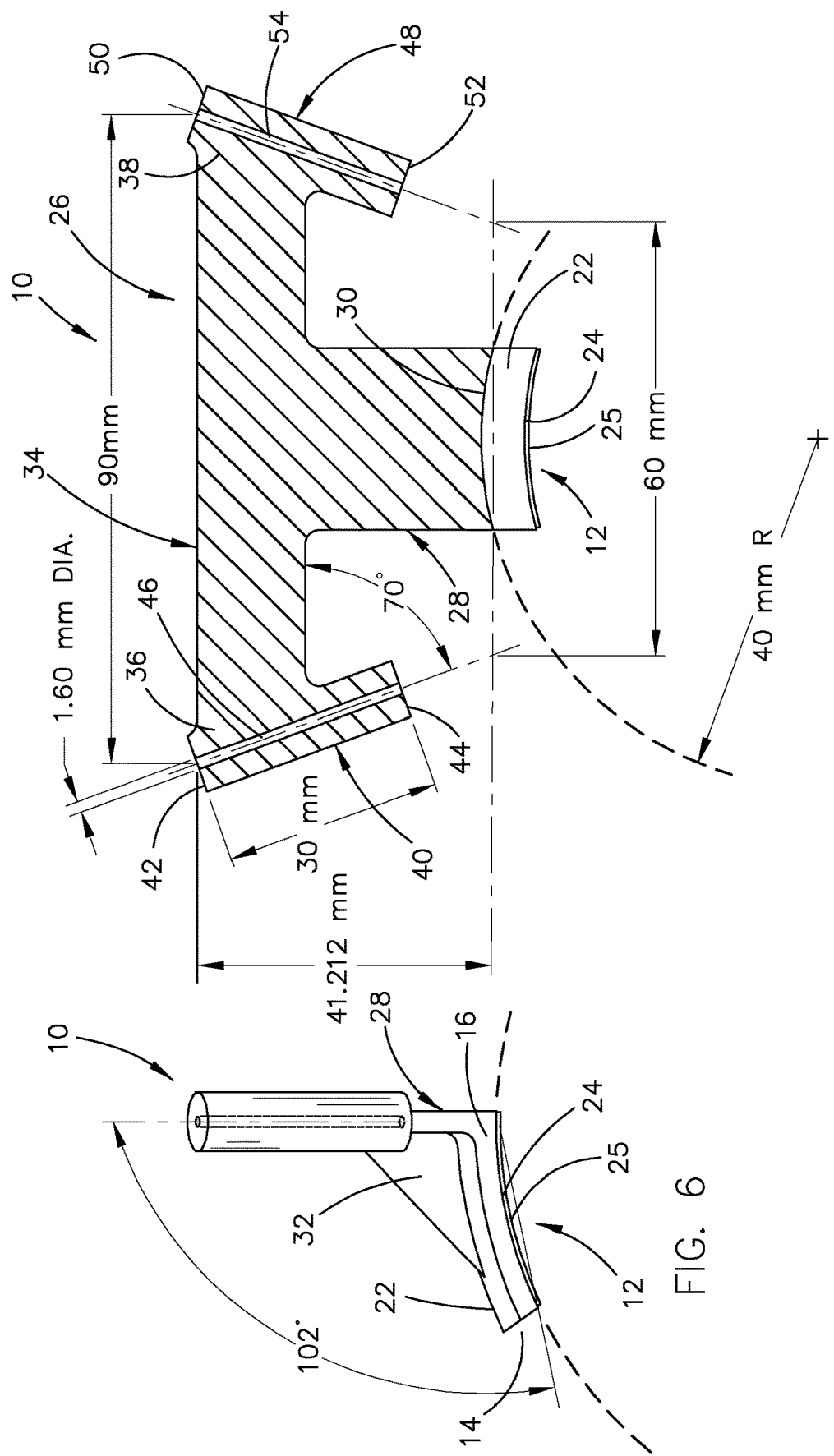

VENTRICULAR GUIDE FOR VENTRICULOSTOMY

BACKGROUND OF THE INVENTION

Field of the Invention

This invention relates to a ventricular guide for use in ventriculostomy. More particularly, this invention relates to a guidance device with preset angles of tilt in the fontal and coronal plane to reach the smallest possible ventricle via frontal and occipital approaches.

Description of the Related Art

Free-hand-approach to ventricular catheter placement is a standard surgical procedure that is often performed at the bedside. Though the procedure is straightforward and easy to perform, there is a low but significant failure rate to enter the intended target on the first attempt. Furthermore, if the ventricles are small, the failure rate is higher. In an attempt to solve the problem, a tripod-shaped guidance system was previously provided which was known as Ghajar Guide and which is described in A Guide for Ventricular Catheter Placement. Technical note in J. Neurosurg 63:985-986, 19. This system assumes that a catheter placed in a trajectory perpendicular (90 degrees) to the skull surface will reach the ventricle. However, this assumption is not always accurate because variations in the human calvarium's contour are not entirely spherical. Park Jaechan et al. published their results showcasing calvarial slop affecting the accuracy of the Ghajar Guide. This publication may be found at: https://pubmed.ncbi.mim.nih.qov/265447781.

Another prior art system is the Thomale Guide (https://patents.google.com/patent/DE10200901522984/en?q=Thomale+ventrical+guide&_oq=Thomale+ventrical+guide) Patent #—DE10200901522984, which is a protractor-conductor with a stand that guides the catheter into the ventricle. The angle in the coronal plane and the entry point is determined using prior CT or MRI images and special software. The system has the following disadvantages:

a. Thomale Guide approach for putting a catheter in the ventricle needs calculation of the angle using the software and will need some extra time. In an emergency, this may not be good for the patient;

b. For a successful outcome of ventricular placement, both the angles in the coronal and sagittal plane are required for precision. With this system, the angle is obtained only in the coronal plane and not in the sagittal place affecting accuracy;

c. The support system in Thomale Guide is not a tripod that is intended to keep the probe holder perpendicular to the skull. However, if the skull slope is non-uniform and unusual, the perpendicularity will be lost; and d. Setting the angle on the protractor needs additional time.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

A ventricular guide for use in ventriculostomy is disclosed. The ventricular guide includes a rectangular base plate having an outer end, an inner end, a first side, a second side, an upper side and a lower side, with the base plate being longitudinally curved downwardly from the inner end thereof to the outer end thereof and with the base plate being laterally curved upwardly from the first side thereof towards the center of the base plate and then curved downwardly from the center of the base plate to the second side thereof. The double curvature of the base plate enables the lower side of the base plate to match the curvature of a patient's skull surface in both the coronal and sagittal planes at the operative site.

The guide also includes an upstanding support member having a lower end, an upper end, a first side, a second side, an outer side and an inner side with the upstanding support member extending upwardly from the inner end of the base plate. The guide also includes an upper support member. The upper support member has a first end, a second end, an upper end, a lower end, an inner side and an outer side. The upper support member is secured to the upper end of the upstanding support member midway between the first and second ends of the upper support member so as to extend transversely with respect to the upstanding support member.

The guide also includes a first tubular guide, having an upper end, a lower end and a bore formed therein which extends between the upper and lower ends thereof. The first tubular guide is secured to the first end of the upper support member so as to extend downwardly at an angle, with respect to the upper support member, from its upper end to its lower end, towards the upstanding support member and the base plate.

The guide also includes a second tubular guide having an upper end, a lower end, and a bore formed therein which extends between the upper and lower ends thereof. The second tubular member is secured to the second end of the upper support member so as to extend downwardly at an angle, with respect to the upper support member, from its upper end to its lower end towards the upstanding support member.

The bores of the first and second tubular members are each configured to have one of a catheter, needle or drill bit extending therethrough.

The ventricular guide provides a guidance device with preset angles of tilt in the frontal and coronal plane to reach the smallest possible ventricle by frontal and occipital approaches.

The ventricular guide of this invention represents a vast improvement over the prior art devices.

The principal object of the invention is to provide a ventricular guide, for use in ventriculostomy, having preset angles of tilt in the frontal and coronal plane to reach the smallest possible ventricle by a frontal and occipital approaches.

A further object of the invention is to provide a ventricular guide which enables the precise placement of catheters in small ventricles.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIG. 3 is a top view of the ventricular guide of this invention;

FIG. 4 is a side view of the ventricular guide of this invention;

FIG. 5 is a front view of the ventricular guide of this invention;

FIG. 6 is a side view of the ventricular guide which illustrates the base plate of the ventricular guide engaging a patient's skull which is shown in broken lines; and FIG. 7 is a sectional view of the ventricular guide as seen on lines 7-7 of FIG. 4.

DESCRIPTION OF THE PREFERRED EMBODIMENT

Figure 1:
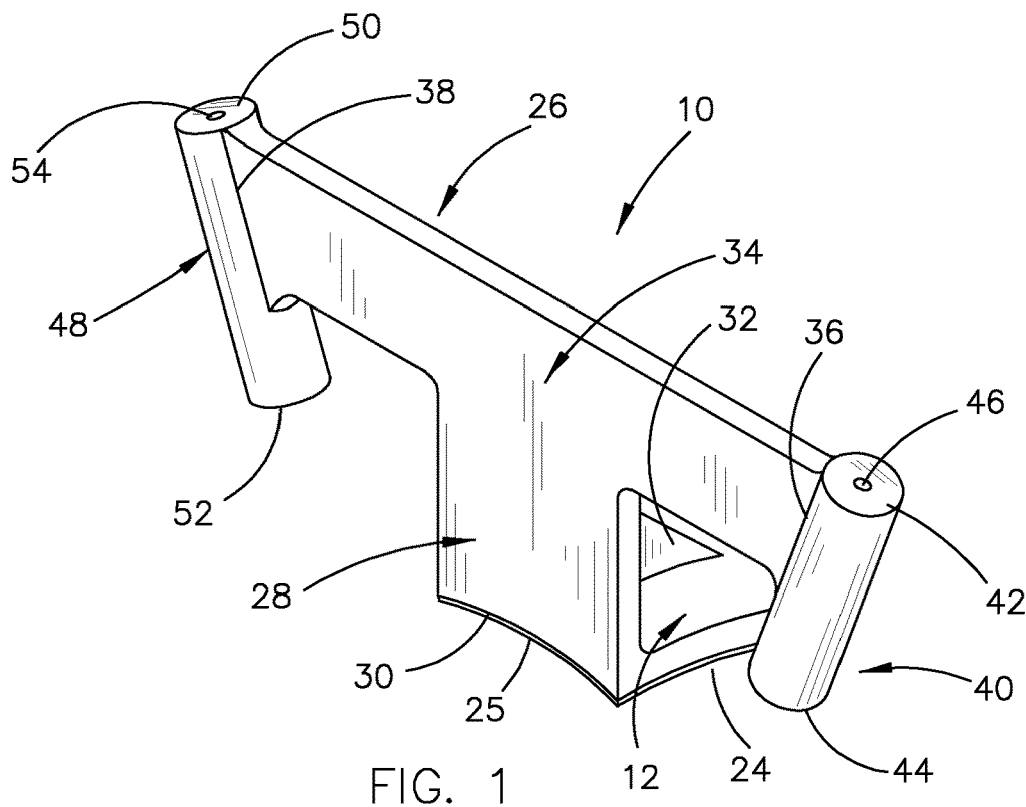
FIG. 1 is a rear perspective view of the ventricular guide of this invention.

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The numeral 10 refers to the ventricular guide of this invention for providing a more accurate and easier access to most sizes of ventricles for ventriculostomy. The guide 10 of this invention may be used to guide drill bits, needles and catheters. The guide 10 will be described as being used in the placement of catheters into the ventricles. The dimensions and angles in the drawings are the preferred dimensions and angles but those dimensions and angles may be varied somewhat as will be described hereinafter.

Guide 10 is preferably comprised of a rigid plastic material but may be comprised of metal if so desired. Guide 10 includes a generally rectangular-shaped base plate 12 having an outer end 14, an inner end 16, a first side 18, a second side 20, an upper side 22 and a lower or bottom side 24. Base plate 12 is curved downwardly from inner end 16 to the outer end 14. Base plate 12 is also curved from the first side 18 to the second side 20. The double curvature of base plate 12 enables the underside or bottom side 24 thereof to conform to the curvature of patient's cranium at the location where the ventriculostomy will be performed. A layer of double-faced adhesive tape material 25 is applied to the bottom side 24 of base plate 12.

Figure 2:
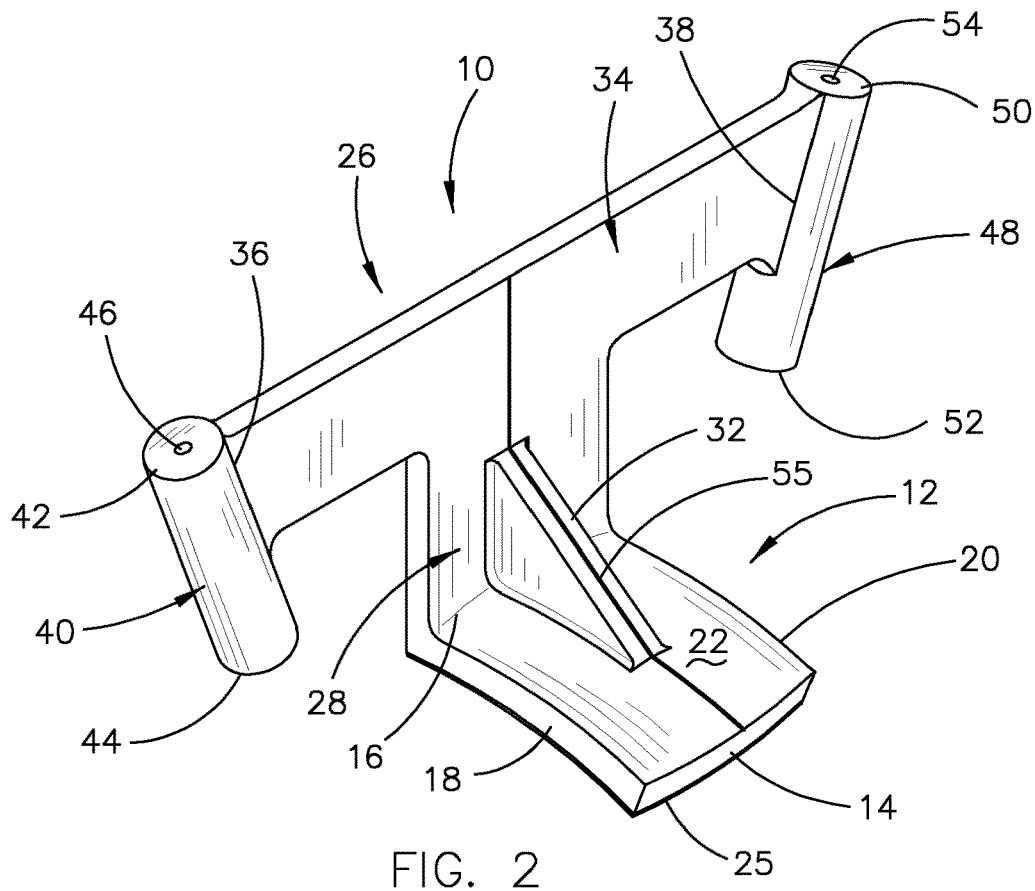
FIG. 2 is a front perspective view of the ventricular guide of this invention.

The numeral 26 refers to a guide support which includes a vertically disposed support member 28 which extends upwardly from the inner end 16 of base plate 12. Support member 28 has a curved lower end 30 which conforms to the side-to-side curvature of base plate 12. A brace 32 extends between the support member 30 and the base plate 12 as best seen in FIG. 2. Guide support 26 also includes an elongated and horizontally disposed support member 34 which extends transversely from the upper end of support member 28. Support member 34 includes a first end 36 and a second end 38.

An elongated guide tube 40 is positioned at end 36 of support member 28 and which has an upper end 42 and a lower end 44. Guide tube 40 has a cannulation or bore 46 extending therethrough. The diameter of bore 46 is preferably from 1.6 mm to 3.2 mm which will accommodate a catheter therein with most catheters having a diameter of 1.2 mm to 2.8 mm. An elongated insert (not shown) may be inserted into bore 46 to accommodate various sizes of catheters. The preferred angle between guide tube 40 and support member 28 as shown in FIG. 7 is 70 degrees plus or minus 10 degrees.

An elongated guide tube 48 is positioned at end 38 of support member 28 and which has an upper end 50 and a lower end 52. Guide tube 48 has a cannulation or bore 54 extending therethrough. The diameter of bore 54 is preferably from 1.6 mm to 3.2 mm which will accommodate a catheter therein with most catheters having a diameter of 1.2 mm to 2.8 mm. An elongated insert (not shown) may be inserted into bore 54 to change the diameter of the bore 54 to accommodate various sizes of catheters. The distance between the upper ends of the bores 46 and 54 of guide tubes 40 and 48 respectively is preferably 90 mm as seen in FIG. 7. The preferred length of the guide tubes 40 and 48 is 30 mm as also seen in FIG. 7. The device 10 has a midline marker 55 provided therein as seen in the drawings.

The drawings illustrate that the angle between the bore 46 of guide tube 40 and the support member 34 is 70 degrees. That angle could be 60 to 80 degrees. The drawings illustrate the angle between bore 54 of guide tube 48 and support members 34 is 70 degrees. That angle could be 60 degrees to 80 degrees. FIG. 6 illustrates that the angle between the guide tubes 40 and 48 and the curved bore plate 16 is 102 degrees. That angle could be 97 degrees to 107 degrees.

The ventricular guide of this invention provides a more accurate and easy access to most sizes of ventricles for ventriculostomy. The guide 10 of this invention includes a base plate 12 which is contoured to the skull surface of the patient. The guide tubes 40 and 48 are connected to the base plate 120 for the right and left sides of the skull of the patient. The guide tube angles with respect to the base plate 12 ensure the success of the catheter into the ventricle. The guide 10 of this invention may be used for the frontal or occipital approach.

With the frontal approach with guide 10, the device entry point is 3 cm lateral midline and 1 cm anterior to the coronal suture. The lateral tilt for the guide tubes 40 and 48 in the coronal plane is 20 degrees and in the sagittal plane, the anterior is 102 degrees to the curvature of the skull. The probe angles may be changed to accommodate ventriculostomy.

Although the guide 10 is used to insert a catheter into the ventricles, the guide tubes thereof may be used to insert drill bits into the skull so that catheters may be inserted through those drill holes. The guide 10 may also be used to insert needles into the skull of the patient as stated above.

In further summary somewhat, the advantages of the instant invention and the disadvantages of the prior art are as follows: The supporting base plate of the instant invention is placed at the top of the head in the midline, which has lesser probability of having non-uniform or unusual contour. On the other hand, the Ghajar and Thomale guides are placed on the side of the head which can affect their accuracies because the side of the head has a higher probability of having non-uniform or unusual contour. The base plate of the instant invention contours both in the coronal and sagittal plane to fit well on the head's surface, an advantage over the Ghajar Guide. The instant invention has two tubular guides equidistant from the midline which have pre-set angles, in coronal and sagittal planes to place the catheter at the optimal spot in the ventricle irrespective of the size of the ventricles. The two systems described above do not have guidance in the sagittal plane. A thick paper replica of the system (a template) can be directly placed on the CT or MR images before the procedure to confirm that the trajectory is on target with the instant system, which is not possible in the prior art.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

We claim:

1. A ventricular guide, comprising:
   a rectangular base plate having an outer end, an inner end, a first side, a second side, an upper side and a lower side;
   said base plate being longitudinally curved downwardly from said inner end thereof to said outer end thereof;
   said base plate being laterally curved upwardly from said first side thereof towards the center of said base plate and thence curved downwardly from the center of said base plate to said second side thereof;
   the double curvature of said base plate enabling said lower side of said base plate to be adapted to match the curvature of a patient's skull surface in both the coronal and sagittal planes at the operative site;
   an upstanding support member having a lower end, an upper end, a first side, a second side, an outer side and an inner side;
   said upstanding support member extending upwards from the inner end of said base plate;
   an upper support member having a first end, a second end, an upper end, a lower end, an inner side and an outer side;
   said upper support member being secured to said upper end of said upstanding support member midway between said first and second ends of said upper support member so as to extend transversely with respect to said upstanding support member;
   a first tubular guide having an upper end, a lower end and a bore formed therein which extends between said upper and lower ends of said first tubular guide;
   said first tubular guide being secured to said first end of said upper support member so as to extend downwardly at an angle, with respect to said upper support member, from the first tubular guide upper end to the first tubular guide lower end towards said upstanding support member and said base plate;
   a second tubular guide having an upper end, a lower end and a bore formed therein which extends between said upper and lower ends of said second tubular guide; and
   said second tubular guide being secured to said second end of said upper support member so as to extend downwardly at an angle, with respect to said upper support member, from the second tubular guide upper end to the first tubular guide lower end towards said upstanding support member.

2. The ventricular guide of claim 1 wherein said bores of said first and second tubular guides are configured to have a catheter extend therethrough.

3. The ventricular guide of claim 2 wherein said bores of said first and second tubular guides are configured to have a needle extend therethrough.

4. The ventricular guide of claim 2 wherein said bores of said first and second tubular guides are configured to have a drill bit extend therethrough.

5. The ventricular guide of claim 1 wherein said first tubular guide extends downwardly from said first end of said upper support member at an angle of 60 to 80 degrees.

6. The ventricular guide of claim 5 wherein said first tubular guide extends downwardly from said first end of said upper support member at an angle of 70 degrees.

7. The ventricular guide of claim 1 wherein said second tubular guide extends downwardly from said first end of said upper support member at an angle of 60 to 80 degrees.

8. The ventricular guide of claim 5 wherein said second tubular guide extends downwardly from said first end of said upper support member at an angle of 70 degrees.

9. The ventricular guide of claim 1 wherein said upstanding support member extends upwardly from said base plate at an angle of 97 degrees to 107 degrees.

10. The ventricular guide of claim 1 wherein said upstanding support member extends upwardly from said base plate at an angle of 102 degrees.

11. The ventricular guide of claim 1 wherein said lower side of said base plate has a layer of double-faced adhesive tape material applied thereto.

12. A ventricular guide, comprising:
    a rectangular base plate having an outer end, an inner end, a first side, a second side, an upper side and a lower side;
    said lower side of said base plate being curved;
    an upstanding support member having a lower end, an upper end, a first side, a second side, an outer side and an inner side;
    said upstanding support member extending upwardly from the inner end of said base plate;
    an upper support member having a first end, a second end, an upper end, a lower end, an inner side and an outer side;
    said upper support member being secured to said upper end of said upstanding support member midway between said first and second ends of said upper support member so as to extend transversely with respect to said upstanding support member;
    a first tubular guide having an upper end, a lower end and a bore formed therein which extends between said upper and lower ends of said first tubular guide;
    said first tubular guide being secured to said first end of said upper support member so as to extend downwardly at an angle, with respect to said upper support member, from the first tubular guide upper end to the first tubular guide lower end towards said upstanding support member and said base plate;
    a second tubular guide having an upper end, a lower end and a bore formed therein which extends between said upper and lower ends of said second tubular guide; and
    said second tubular guide being secured to said second end of said upper support member so as to extend downwardly at an angle, with respect to said upper support member, from the second tubular guide upper end to the first tubular guide lower end towards said upstanding support member.

13. The ventricular guide of claim 12 wherein said bores of said first and second tubular guides are configured to have a catheter extend therethrough.

14. The ventricular guide of claim 12 wherein said bores of said first and second tubular guides are configured to have a needle extend therethrough.

15. The ventricular guide of claim 12 wherein said bores of said first and second tubular guides are configured to have a drill bit extend therethrough.

16. The ventricular guide of claim 12 wherein said first tubular guide extends downwardly from said first end of said upper support member at an angle of 60 to 80 degrees.

17. The ventricular guide of claim 12 wherein said first tubular guide extends downwardly from said first end of said upper support member at an angle of 70 degrees.

18. The ventricular guide of claim 12 wherein said second tubular guide extends downwardly from said first end of said upper support member at an angle of 60 to 80 degrees.

19. The ventricular guide of claim 12 wherein said second tubular guide extends downwardly from said first end of said upper support member at an angle of 70 degrees.

20. The ventricular guide of claim 12 wherein said upstanding support member extends upwardly from said base plate at an angle of 97 degrees to 107 degrees.

21. The ventricular guide of claim 12 wherein said upstanding support member extends upwardly from said base plate at an angle of 102 degrees.

* * * * *